United States Patent [19]

Leet et al.

[11] Patent Number: 5,795,309
[45] Date of Patent: Aug. 18, 1998

[54] CERVICAL TISSUE SAMPLING AND CONTAINMENT DEVICE

[76] Inventors: Richard A. Leet, 3118 Williamsburg, NW., Warren, Ohio 44485; Deborah L. Rowlands, 2697 Oak Forest Dr., Niles, Ohio 44446

[21] Appl. No.: 891,257

[22] Filed: Jul. 10, 1997

[51] Int. Cl.$^6$ .................................................. A61B 10/00
[52] U.S. Cl. ............................................................ 600/569
[58] Field of Search ............................ 600/562, 569–572; 206/569, 570, 571

[56] References Cited

U.S. PATENT DOCUMENTS

| | | | |
|---|---|---|---|
| 3,890,954 | 6/1975 | Greenspan | 600/572 |
| 4,157,709 | 6/1979 | Schuster et al. | 128/759 |
| 4,324,262 | 4/1982 | Hall | 600/569 |
| 4,628,941 | 12/1986 | Kosasky | 128/759 |
| 5,339,828 | 8/1994 | Keating et al. | 600/569 |
| 5,445,164 | 8/1995 | Worthen et al. | 128/759 |

*Primary Examiner*—Max Hindenburg
*Attorney, Agent, or Firm*—Harpman & Harpman

[57] ABSTRACT

A self-actuated sampling instrument for the collection and short term preservation of cervical tissues for testing purposes by remote laboratory. The sampling and preserving device includes a collection cylinder and a retractable plunger having a sampling brush thereon. A containment enclosure is removably positioned over the collection cylinder providing a sterile transportation container for the tissue sample which is suspended in a preservative solution that is mechanically disposed from within the collection cylinder into the containment enclosure around the sample by the user before transportation to the laboratory.

17 Claims, 4 Drawing Sheets

CERVICAL TISSUE SAMPLING AND CONTAINMENT DEVICE

BACKGROUND OF THE INVENTION

1. Technical Field:

This device relates to collection apparatus for cervical tissue sampling by women at home and the transportation of the samples to an offsite testing facility.

2. Description of Prior Art:

Prior art devices of this type have been developed to sample and transport cervical tissue for testing by using insertion elements with attached sampling media surfaces, see for examples U.S. Pat. Nos. 4,157,709, 4,628,941, and 5,445,164.

In U.S. Pat. No. 4,157,709 a probe for obtaining cervical mucus and processes thereof is disclosed wherein a spring activated flexible shaft with a sampling element attached is extended and retracted from within a tubular sheath that allows for the collection of mucus to be retrieved and tested.

U.S. Pat. No. 4,628,941 is directed to a sampling device that uses a semi-flexible hemispherical cup on the end of a tube so that the cup positions the device over the cervix allowing for internal plunger to be extended for engagement with the cervix for removal and sampling function.

U.S. Pat. No. 5,445,164 shows a tissue sampling device that advances a collection sponge in circular brush for collection of cervical sample from within a support barrel. The retrieved samples on the brush and sponge are then removed from the device and sealed in a separate container to be shipped to a testing facility.

SUMMARY OF THE INVENTION

A self-contained sampling and transportation device for the collection of cervical samples. The device retrieves and then preserves the sample within its retrieving structure by suspending the sample in a preservative solution which is contained within the sampling device. An interlocking containment enclosure assures one-time use and secure seal of the specimen within the collection device for transportation via mail or other means to an offsite testing laboratory.

DESCRIPTION OF THE PREFERRED EMBODIMENT

Figure 1:
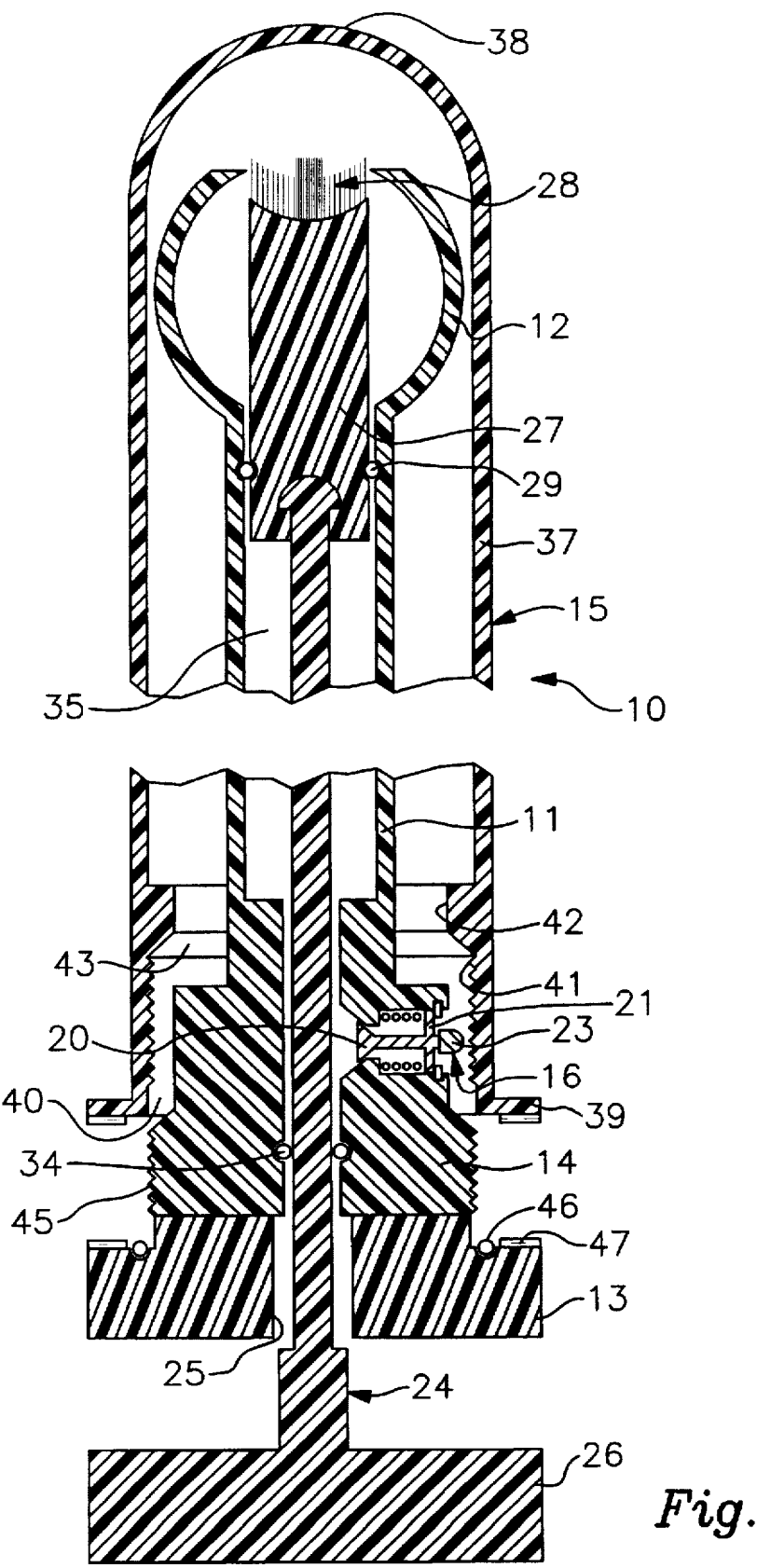
FIG. 1 is a cross-section view with portions broken away of the sampling and transportation device.
Figures 2, 3:
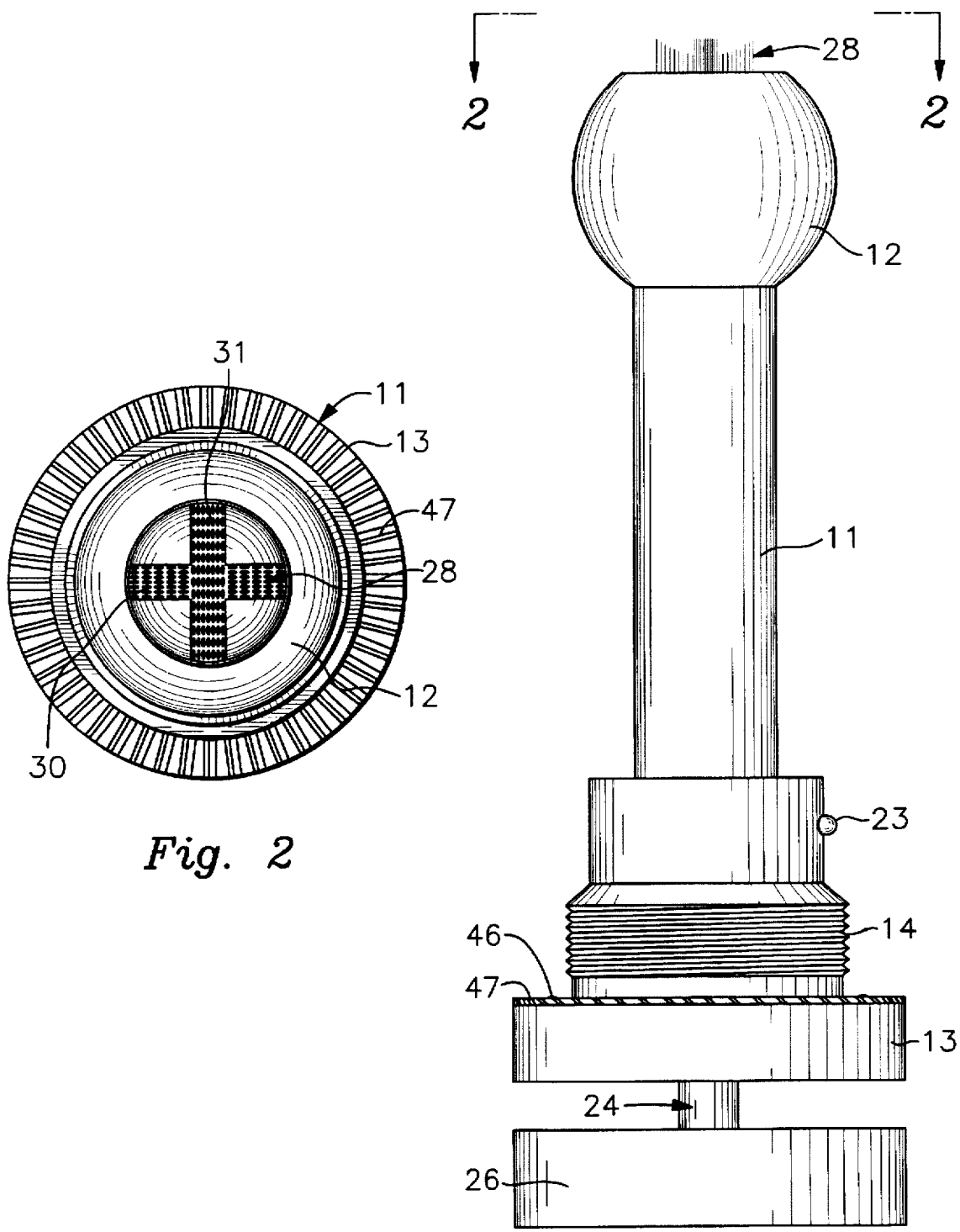
FIG. 2 is an enlarged end plan view of the containment enclosure illustrating the interlocking one-way teeth.
FIG. 3 is a side elevational view of the collection cylinder and sampling brush.

Referring to FIGS. 1–3 of the drawings, a cervical sampling and transportation device 10 can be seen including an elongated rigid collection cylinder 11 having an annular flanged end fitting 13 and an enlarged bulboused end 12 with a circular opening therein at its distal end. The collection cylinder 11 has a threaded area of increased diameter at 14 adjacent the end fitting 13 to receive a containment closure 15. The collection cylinder 11 is preferably formed from ultra pure teflon TFE tubing having a derometer; shore of 60–65, applicant to clean room applications.

A valve assembly 16 is positioned in an opening in the collection cylinder 11's area of increased diameter at 14 so as to provide selective communication with the interior of the collection cylinder 11.

Figure 4:
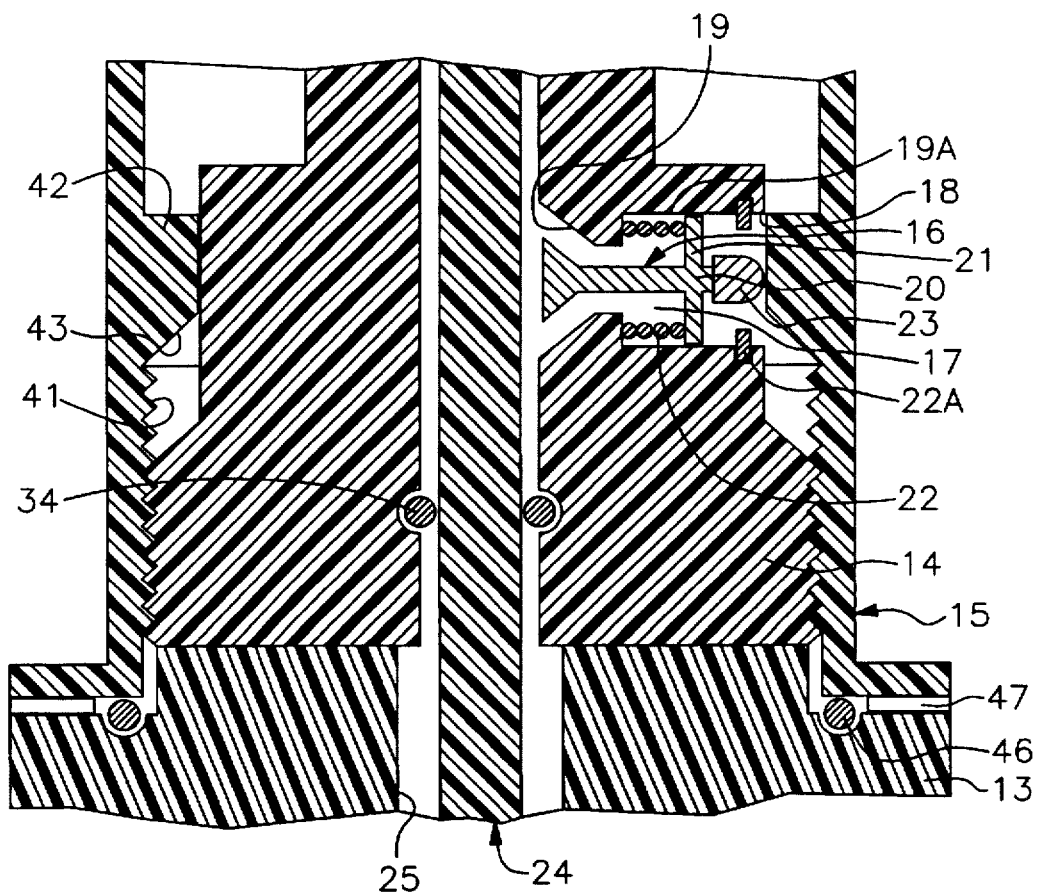
FIG. 4 is an enlarged partial cross-sectional view of the transfer valve in open position.
Figure 5:
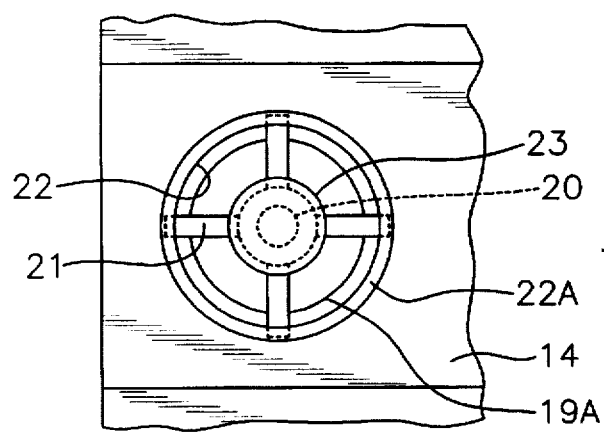
FIG. 5 is an enlarged partial top plan view of the transfer valve shown in FIG. 4.
Figure 6:
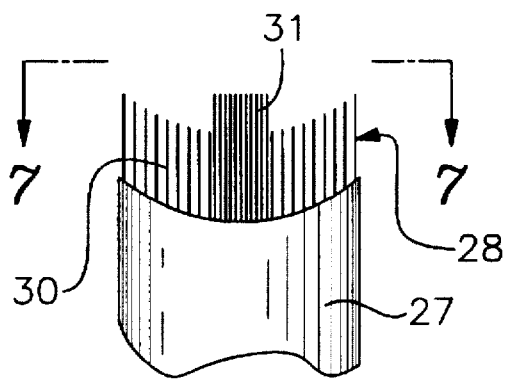
FIG. 6 is an enlarged side elevational view of the sampling brush of the invention.
Figure 7:
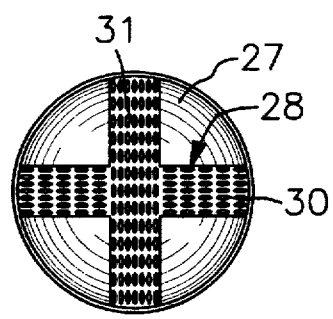
FIG. 7 is an enlarged top plan view of the sampling brush of the invention.
Figure 8:
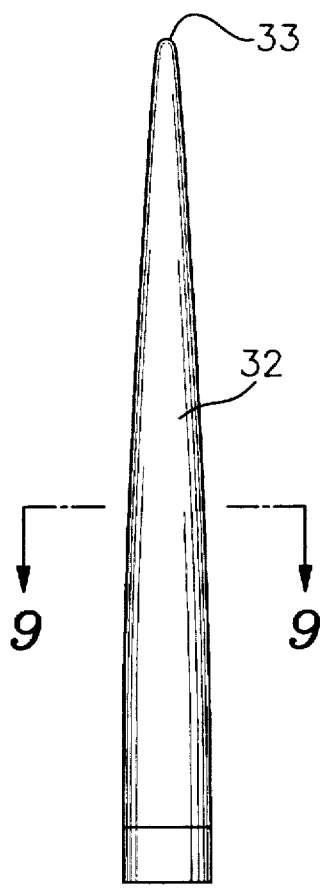
FIG. 8 is an enlarged side elevational view of the sampling brush bristles.
Figure 9:
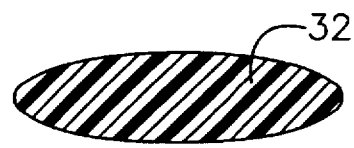
FIG. 9 is a cross-section on lines 9—9 of FIG. 8.

Referring to FIGS. 4 and 5 of the drawings, the valve assembly 16 has a valve chamber 17 with an opening at 18 and an oppositely disposed annular valve seat at 19. A valve element 20 extends from within the valve chamber 17 and has a spring retaining element 21 with a spring 22 and a spring retaining ring 22A and an engagement head 23 on its distal end extending through the opening at 18 hereinbefore described. A sampling plunger 24 extends from within collection cylinder 11 through a bore 25 and has an activation knob 26 on its extended end. A collection fitting 27 is selectively secured to the plunger's free end with a compound collection brush 28 formed thereon as best seen in FIGS. 1 and 6–9 of the drawings. The collection fitting 27 has an O-ring 29 thereon for sealing engagement with the interior of the collection cylinder 11. The collection brush 28 is formed of two intersecting sets 30 and 31 of resilient brush bristles 32 each of which is tapered from its base to a blunted end at 33. The individual bristles 32 are cross-sectionally ovaloid as best seen in FIG. 9 of the drawings. The bristle sets 30 and 31 define curvalineal engagement surfaces to conform to the natural shape of the human cervix (not shown) onto which they are to be engaged while providing segmental bristle engagement for maximized sampling of the surface.

The area of increased diameter at 14 has an O-ring seal 34 thereon for sealing engagement within the plunger 24 which in combination with the O-ring 29 on the collection fitting 27 forms a fluid retaining chamber 35 within the collection cylinder 11 around the sampling plunger 24 which is filled with a specimen preserving solution 36 sold under the trade name "PreservCyt"® a registered trademark of Cytyc Corporation.

Referring back to FIGS. 1, 2, and 4 of the drawings, the containment closure 15 can be seen having an elongated thin wall cylindrical body member 37 with a closed end at 38 and an oppositely disposed annual locking flange 39 around an opening at 40.

The inner surface of the containment closure 15 is internally threaded at 41 inwardly from the opening at 40 terminating at an internal annual flange 42. The flange 42 has a tapered portion 43 that is registerable with the valve element upstanding activation head 23 as the containment closure 15 is threadably advanced onto a threaded surface 45 of the area if increased diameter at 14, best seen in FIG. 4 of the drawings, depressing the valve element 20, opening same.

The containment closure 15 seals and locks against a resilient sealing ring 46 on the flanged end fitting 13 by engagement of interlocking one-way teeth 47 on the respective flange fitting 13 and annular locking flange 39 thereby restricting removal of the containment closure 15 from the collection cylinder 11 as will be well understood by those skilled in the art.

In use, the containment closure 15 when shipped to the user is not fully engaged on the collection cylinder 11 and therefore can be removed from the collection cylinder 11 for use. The plunger 24 is then pushed inwardly advancing the attached collection fitting 27 from within the bulbous end 12 of the collection cylinder 11. After insertion, the female user rotates the collection fitting 27 and the integrally attached brush assembly 28 by rotation of the plunger knob 26 retrieving a tissue sample (not shown) onto the brush assembly for testing purposes. The device is then withdrawn from the female user and the containment closure is re-positioned on and over the collection cylinder 11 by threadably engaging and advancing onto the collection cylinder 11 into the locked sealed position against the sealing ring 46 on the end fitting 13 and interengagement of the corresponding one-way teeth 46 as hereinbefore described.

As the containment closure 15 is advanced onto the collection cylinder 11 the annular flange 42 engages and opens the valve assembly 16. After confirmation that the containment closure 15 has sealingly engaged, the plunger 24 is pulled outwardly via the knob 26 which displaces the preservative solution 36 within the chamber 35 through the valve assembly 16 into the containment closure 15 enveloping the sample brush 28 and collected specimen thereon. Repeated plunger oscillations will assure that the specimen is immersed within the preservative solution 36.

The sampling device of the invention is then shipped via U.S. mail or other means to an offsite testing laboratory for testing.

It will noted that the sampling device of the invention may be sold as a kit including a mailing container in which to mail or otherwise transport the entire device to the offsite laboratory for testing.

It will evident to those skilled in the art that various changes and modifications may be made thereto without departing from the spirit of the invention.

Therefore I claim:

1. A cervical tissue sampling and transportation device comprising: a collection cylinder, a plunger disposed for reciprocally sliding movement within said cylinder, a first fluid chamber within said collection cylinder, a collection brush secured to a distal end of said plunger, a containment closure removably positioned in sealing relation over a portion of said collection cylinder, a second fluid chamber within said containment closure and a portion of said collection cylinder, means for transferring contents of said first fluid chamber to said second fluid chamber and means for sealing and locking said containment closure onto said collection cylinder.

2. The cervical tissue sampling and transportation device of claim 1 wherein said portion of said collection cylinder disposed about said collection brush is of an enlarged bulbous dimension defining an insertion guide.

3. The cervical tissue sampling and transportation device of claim 1, wherein said collection brush comprises; a plurality of resilient bristles defining a concave engagement end surface.

4. The cervical tissue sampling and transportation device of claim 1 wherein said first fluid chamber contains a preserving solution.

5. The cervical tissue sampling and transportation device of claim 1 wherein said collection cylinder has an area of increased diameter having external threads thereon, and an end fitting with a finger grip flange thereon.

6. The cervical tissue sampling and transportation device of claim 1 wherein said plunger extends from said collection cylinder having an activation knob thereon in spaced relation to said collection cylinder.

7. The cervical tissue sampling and transportation device of claim 1 wherein said means for locking said containment closure onto said collection cylinder comprises; a plurality of interengaging teeth on said containment closure and said collection cylinder.

8. The cervical tissue sampling and transportation device of claim 1 wherein said means for transferring contents of said first fluid chamber to said second fluid chamber comprises; a valve assembly in said collection cylinder and valve actuation means in said containment closure.

9. The cervical tissue sampling and transportation device of claim 8 wherein said valve assembly comprises; a valve chamber, a valve seat in said chamber, a valve element registerable within said valve seat, spring means engageable on said valve element, said valve element having a activation head thereon.

10. The cervical tissue sampling and transportation device of claim 8 wherein said valve actuation means comprises; an internal annular flange in said containment closure registerable with said valve assembly when in sealing relationship on said collection cylinder.

11. The cervical tissue sampling and transportation device of claim 1 further comprises; sealing means between said plunger and collection cylinder defining said first fluid chamber.

12. A cervical tissue sampling and transportation device comprising; a collection cylinder, a plunger disposed for reciprocally sliding movement within said collection cylinder, a collection fitting and brush secured to the distal end of said plunger within said collection cylinder, a first fluid chamber within a portion of said collection cylinder, a containment closure threadably secured over said collection cylinder defining a second fluid chamber about and in a portion of said collection cylinder, said collection brush within said portion of said collection cylinder within said second fluid chamber, sealing means within said collection cylinder defining said first fluid chamber, valve means interconnecting said first fluid chamber with said second fluid chamber, and means for fluid transfer between said first and second fluid chambers.

13. The cervical tissue sampling and transportation device of claim 12 wherein said collection brush comprises; sets of resilient bristles.

14. The cervical tissue sampling and transportation device of claim 13 wherein said bristle sets form concave engagement end surfaces.

15. The cervical tissue sampling and transportation device of claim 13 wherein said bristles are tapered and cross-sectionally ovaloid.

16. The cervical tissue sampling and transportation device of claim 13 wherein said bristles are formed of synthetic resin material.

17. The cervical tissue sampling and transportation device of claim 13 wherein said means for fluid transfer between said first and second fluid chambers comprises; said collection fitting on said plunger and said sealing means within said collection cylinder.

* * * * *